United States Patent [19]

Rawlings et al.

[11] Patent Number: 4,748,118

[45] Date of Patent: * May 31, 1988

[54] **CONSTRUCTION OF ARSENIC RESISTANCE VECTORS FOR *THIOBACILLUS FERROOXIDANS***

[75] Inventors: Douglas E. Rawlings; David R. Woods, both of Rondebosch, South Africa

[73] Assignee: General Mining Union Corporation Limited, Johannesburg, South Africa

[*] Notice: The portion of the term of this patent subsequent to Dec. 8, 2004 has been disclaimed.

[21] Appl. No.: 667,259

[22] Filed: Nov. 1, 1984

[51] Int. Cl.$^4$ ............... C12N 15/00; C12N 1/20; C12N 7/00
[52] U.S. Cl. ................... 435/172.3; 435/253; 435/320; 435/849; 435/281; 935/29; 935/56
[58] Field of Search .................. 435/172.3, 317, 253; 935/14, 29

[56] References Cited

U.S. PATENT DOCUMENTS 4,340,674  7/1982  Monis et al. ................ 425/172

FOREIGN PATENT DOCUMENTS 3116648  11/1982  Fed. Rep. of Germany ........ 74/600
2512058   4/1983  France ........................ 528/25
3709      4/1984  South Africa .

OTHER PUBLICATIONS

Chemical Abstracts 95:3291t–1981, (Anthony M. Brown and Neil S. Willets, Plasmid, 1981, 5(2), 188–201).

Chemical Abstracts 101:145108e, 1984, (Nicolau, Claude et al.).

Kreft, J. et al., Mol. Gen. Genet., 1983, pp. 384–389.

Rawlings, D. E. et al., Abstract in French of International Symposium on Biohydrometallurgy, May 1, 1983, pp. 555–570.

Rawlings, D. E. et al., "Expression of *Thiobacillus ferrooxidans* Origin of Replication in *Escherichia coli*", Journal of Bacteriology, vol. 158, No. 2, May, 1984, pp. 737–738.

Rawlings, D. E. et al, "Construction of Arsenic–Resistant *Thiobacillus ferrooxidans* Recombinant Plasmids and the Expression of Autotrophic Plasmid Genes in a Heterotrophic Cell–Free System", Journal of Biotechnology, 1 (1984), 129–133.

Brown, Anthony M. C. et al., "A Physical and Genetic Map of the IncN Plasmid R46", Plasmid 5, 188–200 (1981).

Holmes et al., J. Bacteriol., 157(1): 324–326, 1984 (Jan.).

Martin et al., Con. J. Microbiol., 27:850–853, 1981.

Summers et al., In. Microbiology–1978, (ed. Schlessinger) A.S.M., 1978, pp. 128–131.

Primary Examiner—Thomas G. Wiseman
Assistant Examiner—Thomas D. Mays

[57] ABSTRACT

A process for constructing the plasmids pDR416 and pDR420 which contain arsenic resistance genes and which are able to replicate in both *T. ferroxidans* and *E. coli* comprises preparing a recombinant of pBR325 or the like and a *T. ferroxidans* plasmid, forming a deletion plasmid and inserting arsenic resistance genes e.g. from R46 by EcoR1 excision and ligation.

14 Claims, 2 Drawing Sheets

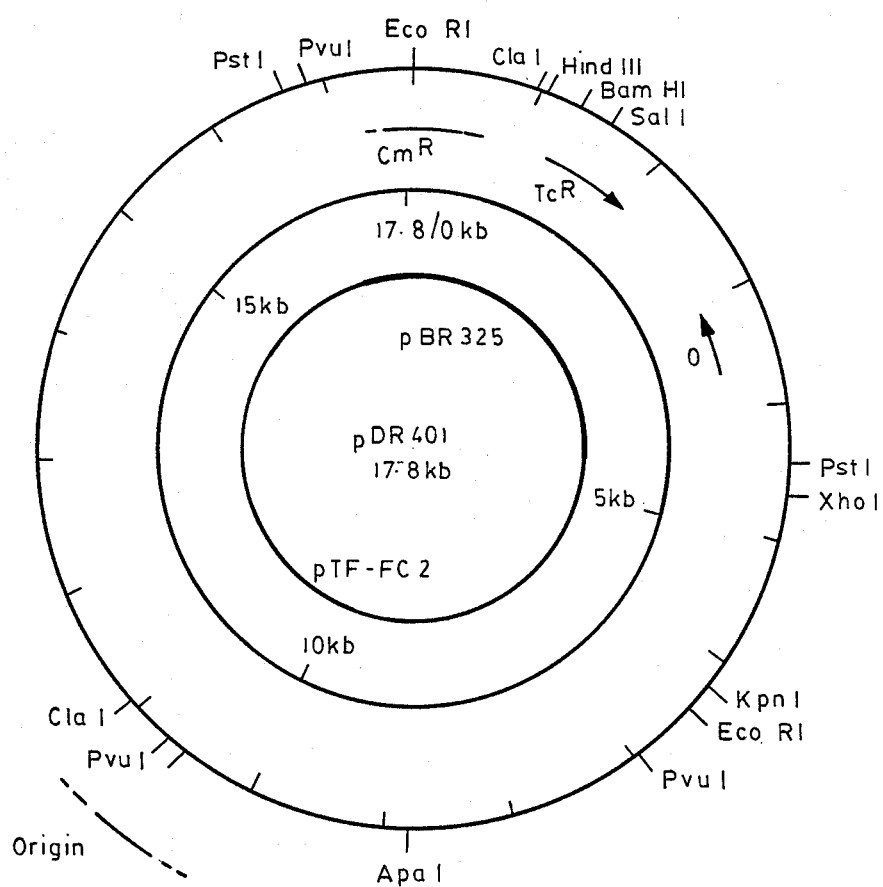
FIG_1

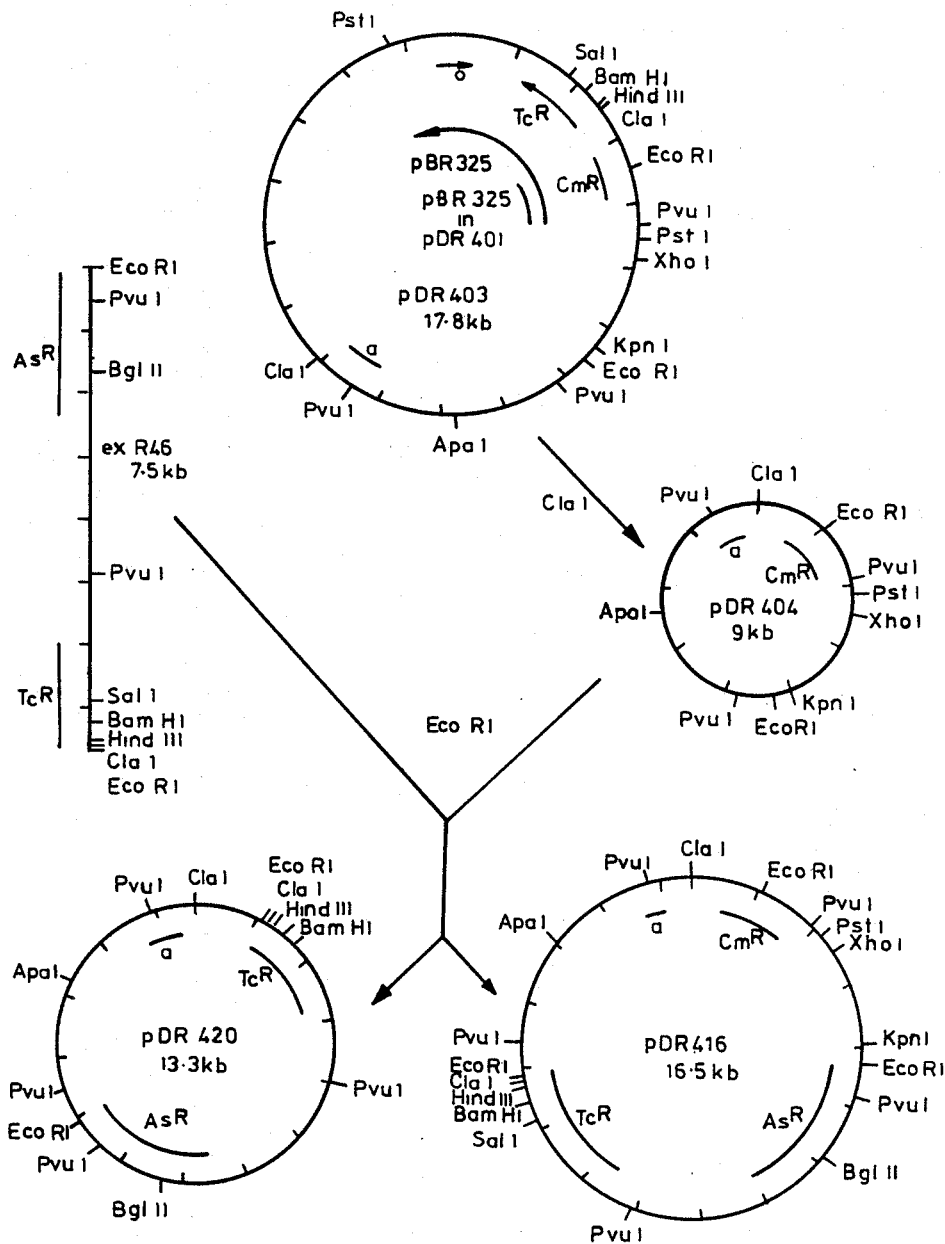
FIG_2

CONSTRUCTION OF ARSENIC RESISTANCE VECTORS FOR *THIOBACILLUS FERROOXIDANS*

BACKGROUND OF THE INVENTION

This invention relates to the construction of recombinant DNA plasmid vectors for *Thiobacillus ferrooxidans* which contain arsenic resistance genes and are able to replicate in both *T. ferrooxidans* and *Escherichia coli*.

The biological leaching of arseno-pyrite ores has hitherto been limited by the sensitivity of the organisms involved to the arsenic which is released in the process.

Although arsenic resistant plasmids have been constructed for other bacteria, there are to the applicant's knowledge no reports of the construction of such plasmids for *T. ferrooxidans* which can also replicate in *E. coli*.

SUMMARY OF THE INVENTION

According to the present invention a DNA plasmid is constructed which contains arsenic resistance genes and can replicate in *T. ferrooxidans*. These plasmids can be transformed into *T. ferrooxidans* and enhance the arsenic resistance of the recipients.

The method is preferably carried out by cleaving a cryptic DNA plasmid from a *T. ferrooxidans* strain and a second plasmid with the same restriction enzyme, ligating the plasmids to form a recombinant plasmid, removing the *E. coli* origin of replication from the recombinant plasmid to form a deleted recombinant plasmid, removing arsenic resistance genes from a third plasmid by cleaving with a restriction enzyme, and inserting the genes into the deleted recombinant plasmid by cleaving with the same restricton enzyme thereby to generate the arsenic resistance plasmids.

The invention also extends to an arsenic plasmid pDR416 which has a size of about 16.5 kb and which is divided into five fragments having the sizes 4.4 kb, 3.6 kb, 3.4 kb, 2.8 kb and 2.3 kb, respectively by the restriction enzyme Pvu1.

The invention further extends to an arsenic resistance plasmid pDR420 which has a size of about 13.3 kb and which is divided into four fragments having the sizes 4.4 kb, 4.2 kb, 3.6 kb and 1.1 kb, repectively by the restriction enzyme Pvu1.

The plasmids of the invention find use in the leaching of ores, particularly in gold recovery processes.

DESCRIPTION OF THE INVENTION

An example of the invention is described with reference to the accompanying drawings in which:

FIG. 1 illustrates restriction maps of plasmids pTF-FC2 and pDR401, and

FIG. 2 illustrates restriction maps of plasmids pDR403, pDR404, pDR416 and pDR420, and an R46 fragment.

A 12.4 kilobase (kb) cryptic plasmid, pTF-FC2, was extracted from a *T. ferrooxidans* FC strain isolated from acid leach liquor from Fairview Mine, General Mining Union Corporation Limited, South Africa. Restriction mapping of pTF-FC2 shows that it has unique Pst1, Xho1, Kpn1, EcoR1, Apa1, Cla1 restriction sites, and two Pvu1 restriction sites, refer to FIG. 1.

A recombinant plasmid, pDR401 was constructed by insertion of the *E. coli* plasmid, pBR325, into the Pst1 site of pTF-FC2. pBR325 contains the genes for ampicillin (Ap), chloramphenicol (Cm) and tetracycline (Tc) resistance. Cloning at the Pst1 site insertionally inactivated the $Ap^R$ gene and *E. coli* transformants which were $Cn^R$, $Tc^R$ and $Ap^S$ were isolated. The recombinant plasmid pDR401 (about 17.8 kb) was extracted from the *E. coli* transformants and characterized by restriction analysis. This novel recombinant plasmid contains the genes for $Cm^R$ and $Tc^R$ and is able to replicate in *T. ferrooxidans* and *E. coli*.

It is possible, though, depending on the orientation of insertion of the plasmid pBR325, to construct the plasmid pDR401 (17.8 kb), or the plasmid pDR403 (17.8 kb) a restriction map of which is shown in FIG. 2. (It should be pointed out at this stage that other suitable plasmids could possibly be used in place of pBR325).

In accordance with the present invention the *E. coli* origin of replication is removed from the pDR403 plasmid to form the deleted recombinant plasmid pDR404 (9 kb) (see FIG. 2).

Aresenic resistance genes are removed from the plasmid R46, a 7.5 kb fragment containing the $As^R$ and $Tc^R$ genes, which is an EcoR1 digest of the IncN plasmic R46 (Brown & Willets 1981). This is done by cleaving the R46 plasmid with the restriction enzyme EcoR1. The arsenic resistance genes are inserted into the plasmid pDR404, by cleaving with the same restriction enzyme EcoR1, to generate the arsenic resistance plasmids pDR416 and pDR420.

Each of the plasmids pDR416 (16.5 Kb) and pDR420 (13.3 kb) was characterized by endonucleolytic cleavage with the restriction enzyme Pvu1.

The plasmid pDR416 is, in this way, cleaved into five fragments having the sizes 4.4 kb, 3.6 kb, 3.4 kb, 2.8 kb and 2.3 kb, respectively.

The plasmid pDR420 is cleaved by the same enzyme into four fragments having the sizes 4.4 kb, 4.2 kb, 3.6 kb and 1.1 kb, respectively.

*T. ferrooxidans* strains into which the plasmids of the invention have been transformed are utilized for the leaching of arseno-pyritic ores and the consequent enhanced extraction of minerals therefrom.

In one process known to the applicant gold ore is exposed to arseno-pyrite and as the gold is released for extraction the arsenic goes into solution. The arsenic concentration builds up and this inhibits the organism thereby minimizing the extraction efficiency. The problem is countered by precipitating the arsenic at regular intervals and continuing the process with a fresh solution. The result is that the process is time consuming and expensive.

The plasmids of the invention are arsenic resistant and, transformed into the *T. ferrooxidans* strains enable the accelerated leaching of the ores. This results because the time interval before arsenic precipitation is required, if at all, is increased.

The *T. ferrooxidans* strain has been deposited with the American Type Culture Collection, 12301 Parklawn Drive, Rockville, MD 20852 and has been assigned ATCC number 39838. It has a taxonometric description follows: It is an autotrophic aerobic, Gram-negative, rod shped bacterium. It is able to oxidize ferrous iron to ferric iron and reduced and partially reduced sulfur compounds to sulfuric acid. Its optimum pH is between 1.6 and 2.2 its optimum temperature is between 25° C. and 30° C. It has a G-C ratio of 59–60 mol percent.

We claim:

1. A method of constructing arsenic resistance vectors for *Thiobacillus ferrooxidans* which includes the steps of;

(a) cleaving a cryptic DNA plasmid from a *T. ferrooxidans* strain with a first restriction enzyme, cleaving a second plasmid containing an *E. coli* origin of replication with the same first restriction enzyme and ligating the plasmids to form a recombinant plasmid, (b) transforming *E. coli* cells with said recombinant plasmid and selecting for transformants, (c) removing the *E. coli* origin of replication from said recombinant plasmid to form a deleted recombinant plasmid, (d) removing at least one arsenic resistance gene from a third plasmid by cleaving said third plasmid with a second restriction enzyme, cleaving the deleted recombinant plasmid with the same second restriction enzyme and ligating said arsenic resistance gene to said deleted recombinant plasmid plasmid to generate an arsenic resistance recombinant plasmid;

(e) transforming *T. ferrooxidans* cells with the arsenic resistance recombinant plasmid and selecting for transformants, and, (f) isolating said arsenic resistance recombinant plasmid.

2. A method of constructing arsenic resistance vectors for *Thiobacillus ferrooxidans* including the steps of cleaving with the same restriction enzyme a cryptic, wild type DNA plasmid from a *T. ferrooxidans* strain and a second plasmid containing an *E. coli* origin of replication and antibiotic-resistance genes; ligating the plasmids to form a recombinant plasmid; removing from said recombinant plasmid the *E. coli* origin of replication and one of the antibiotic resistance genes by deletion; cleaving with restriction enzyme the resultant deleted plasmid and a third plasmid containing an arsenic resistance gene, and ligating said arsenic-resistance gene from the third plasmid to the deleted plasmid or to a portion thereof containing the *T. ferrooxidans* origin of replication.

3. A method according to claim 1 wherein the cryptic DNA plasmid is pTF-FC2 and has the size 12.4 kb.

4. A method according to claim 1 wherein the second plasmid is pBR325.

5. A method according to claim 1 wherein the recombinant plasmid is pDR403 and has the size of 17.8 kb.

6. A method according to claim 1 wherein the deleted recombinant plasmid is pDR404 and has the size 9 kb.

7. A method according to claim 1 wherein the third plasmid is R46 and has the size of 7.5 kb and contains arsenic resistance genes.

8. A method according to claim 1 wherein the third plasma is cleaved with the EcoR1 restriction enzyme.

9. An arsenic resistance plasmid constructed by the method of claim 1.

10. The arsenic resistance plasmid pDR416 which has a size of about 16.5 kb and which is divided into five fragments having the sizes 4.4 kb, 3.6 kb, 3.4 kb and 2.3 kb, respectively when said plasmid is cleaved by the restriction enzyme Pvu1.

11. The arsenic resistance pDR420 which has size of about 13.3 kb and which is divided into four fragments having the sizes 4.4 kb, 4.2 kb, 3.6 kb and 1.1 kb, respectively when said plasmid is cleaved by the restriction enzyme Pvu1.

12. A transformed host of *Thiobacillus ferrooxidans* containing the plasmid of claim 9.

13. A transformed host of *Thiobacillus ferrooxidans* containing the plasmid of claim 10.

14. A transformed host of *Thiobacillus ferrooxidans* containing the plasmid of claim 11.

* * * * *

UNITED STATES PATENT AND TRADEMARK OFFICE
CERTIFICATE OF CORRECTION

PATENT NO. : 4,748,118

DATED : May 31, 1988

INVENTOR(S) : Douglas E. Rawlings and David R. Woods

It is certified that error appears in the above-identified patent and that said Letters Patent is hereby corrected as shown below:

On the cover page under "OTHER PUBLICATIONS", "Con. J. Microbiol." should be --Can. J. Microbiol.-- and "In. Microbiology" should be --Microbiology--.

Claim 1 (column 3, line 17), "plasmid plasmid" should be --plasmid--.

Claim 8 (column 4, line 16), "plasma" should be --plasmid--.

Claim 11 (column 4, line 25), after "resistance" insert --plasmid--.

Signed and Sealed this

Eighteenth Day of October, 1988

Attest:

DONALD J. QUIGG

*Attesting Officer*  *Commissioner of Patents and Trademarks*